(12) United States Patent
Pahl

(10) Patent No.: US 6,686,153 B1
(45) Date of Patent: Feb. 3, 2004

(54) PRV-1 GENE AND THE USE THEREOF

(75) Inventor: Heike Pahl, Freiburg (DE)

(73) Assignee: Universitatsklinikum Freiburg, Freiburg (DE)

( * ) Notice: Subject to any disclaimer, the term of this patent is extended or adjusted under 35 U.S.C. 154(b) by 0 days.

(21) Appl. No.: 09/830,189

(22) PCT Filed: Sep. 30, 1999

(86) PCT No.: PCT/EP99/07238

§ 371 (c)(1),
(2), (4) Date: Aug. 6, 2001

(87) PCT Pub. No.: WO00/24886

PCT Pub. Date: May 4, 2000

(30) Foreign Application Priority Data

Oct. 23, 1998 (DE) .......................................... 198 49 044

(51) Int. Cl.⁷ ........................ C07K 14/435; C12N 1/21; C12N 5/10; C12N 15/12; C12N 15/63
(52) U.S. Cl. ........................ 435/6; 536/23.1; 536/23.5; 530/350; 530/300; 514/2; 514/12; 435/69.1; 435/320.1; 435/325; 435/252.3
(58) Field of Search ................................ 536/23.1, 23.5; 530/350, 300; 435/320.1, 325, 252.3, 254.11, 6, 69.1; 514/2, 12

(56) References Cited

U.S. PATENT DOCUMENTS 6,084,088 A * 7/2000 Sheppard et al.

OTHER PUBLICATIONS

Temerinac et al., 2000, Blood 95:2569–2576.*
Klippel et al., 2002, Blood 100:2441–2448.*
Pahl, 2000, Eur. J. Biochem. 267:3395–3401.*
Wells, 1990, Biochemistry 29:8509–8517.*
Ngo et al., 1994, The Protein Folding Problem and Tertiary Structure Prediction, Merz et al., eds., Birkhauser, Boston, pp. 492–495.*

* cited by examiner

*Primary Examiner*—Elizabeth Kemmerer
(74) *Attorney, Agent, or Firm*—Millen, White, Zelano & Branigan

(57) ABSTRACT

This document describes a nucleotide sequence which encodes the PRV-1 protein, and essentially comprises the sequence ID No. 1, and also a process for detecting this gene and the polypeptide encoded by this gene.

21 Claims, 2 Drawing Sheets

```
AAAAGCAGAAAGAGATTACCAGCCACAGACGGGTCATGAGCGCGGTATTACTGCTGGCCCTCC
TGGGGTTCATCCTCCCACTGCCAGGAGTGCAGGCGCTGCTCTGCCAGTTTGGGACAGTTCAGC
ATGTGTGGAAGGTGTCCGACCTGCCCCGGCAATGGACCCCTAAGAACACCAGCTGCGACAGCG
GCTTGGGGTGCCAGGACACGTTGATGCTCATTGAGAGCGGACCCCAAGTGAGCCTGGTGCTCT
CCAAGGGCTGCACGGAGGCCAAGGACCAGGAGCCCCGCGTCACTGAGCACCGGATGGGCCCCG
GCCTCTCCCTGATCTCCTACACCTTCGTGTGCCGCCAGGAGGACTTCTGCAACAACCTCGTTA
ACTCCCTCCCGCTTTGGGCCCCACAGCCCCCAGCAGACCCAGGATCCTTGAGGTGCCCAGTCT
GCTTGTCTATGGAAGGCTGTCTGGAGGGGACAACAGAAGAGATCTGCCCCAAGGGGACCACAC
ACTGTTATGATGGCCTCCTCAGGCTCAGGGGAGGAGGCATCTTCTCCAATCTGAGAGTCCAGG
GATGCATGCCCCAGCCAGGTTGCAACCTGCTCAATGGGACACAGGAAATTGGGCCCGTGGGTA
TGACTGAGAACTGCAATAGGAAAGATTTTCTGACCTGTCATCGGGGGACCACCATTATGACAC
ACGGAAACTTGGCTCAAGAACCCACTGATTGGACCACATCGAATACCGAGATGTGCGAGGTGG
GGCAGGTGTGTCAGGAGACGCTGCTGCTCATAGATGTAGGACTCACATCAACCCTGGTGGGGA
CAAAAGGCTGCAGCACTGTTGGGGCTCAAAATTCCCAGAAGACCACCATCCACTCAGCCCCTC
CTGGGGTGCTTGTGGCCTCCTATACCCACTTCTGCTCCTCGGACCTGTGCAATAGTGCCAGCA
GCAGCAGCGTTCTGCTGAACTCCCTCCCTCCTCAAGCTGCCCCTGTCCCAGGAGACCGGCAGT
GTCCTACCTGTGTGCAGCCCCTTGGAACCTGTTCAAGTGGCTCCCCCCGAATGACCTGCCCCA
GGGGCGCCACTCATTGTTATGATGGGTACATTCATCTCTCAGGAGGTGGGCTGTCCACCAAAA
TGAGCATTCAGGGCTGCGTGGCCCAACCTTCCAGCTTCTTGTTGAACCACACCAGACAAATCG
GGATCTTCTCTGCGCGTGAGAAGCGTGATGTGCAGCCTCCTGCCTCTCAGCATGAGGGAGGTG
GGGCTGAGGGCCTGGAGTCTCTCACTTGGGGGGTGGGGCTGGCACTGGCCCCAGCGCTGTGGT
GGGGAGTGGTTTGCCCTTCCTGCTAACTCTATTACCCCCACGATTCTTCACCGCTGCTGACCA
CCCACACTCAACCTCCCTCTGACCTCATAACCTAATGGCCTTGGACACCAGATTCTTTCCCAT
TCTGTCCATGAATCATCTTCCCCACACACAATCATTCATATCTACTCACCTAACAGCAACACT
GGGGAGAGCCTGGAGCATCCGGACTTGCCCTATGGGAGAGGGGACGCTGGAGGAGTGGCTGCA
TGTATCTGATAATACAGACCCTGTC
```

Fig. 1

```
MSAVLLLALLGFILPLPGVQA---LLCQFGTVQHVWKVSDLPRQWTPKNTSCD
SGLGCQDTLMLIESGPQVSLVLSKGCTEAKDQEPRVTEHRMGPGLSLISY
TFVCRQEDFCNNLVNSLPLWAPQPPADPGSLRCPVCLSMEGCLEGTTEEI
CPKGTTHCYDGLLRLRGGGIFSNLRVQGCMPQPGCNLLNGTQEIGPVGMT
ENCNRKDFLTCHRGTTIMTHGNLAQEPTDWTTSNTEMCEVGQVCQETLLL
IDVGLTSTLVGTKGCSTVGAQNSQKTTIHSAPPGVLVASYTHFCSSDLCN
SASSSSVLLNSLPPQAAPVPGDRQCPTCVQPLGTCSSGSPRMTCPRGATH
CYDGYIHLSGGGLSTKMSIQGCVAQPSSFLLNHTRQIGIFSAREKRDVQP
PASQHEGGAEGLESLTWGVGLALAPALWWGVVCPSC
```

Fig. 2

PRV-1 GENE AND THE USE THEREOF

BACKGROUND OF THE INVENTION

The invention relates to a nucleotide sequence which encodes the PRV-1 gene, to recombinant DNA which contains this nucleotide sequence, to vectors which contain the recombinant DNA and to cells which are transformed with these vectors, and also to a PRV-1 polypeptide, to antibodies against this polypeptide, to a process for detecting the PRV-1 polypeptide and to drugs which comprise the PRV-1 polypeptide or antibodies which are directed against the PRV-1 polypeptide.

Polycythaemia rubra vera (erythraemia), also termed polycythaemia vera or p. vera, is a malignant haematological disease in which there is an increased formation of erythroid, granulocytic and megakaryocytic cells. The disease is of clonal origin and arises as a result of the mutation of a single haematopoietic precursor cell. In Germany, the incidence of p. vera is from 4 to 6 per million inhabitants. If left untreated, the disease leads to death within 18 months. Treatment by means of blood-letting or chemotherapy extends the average survival time to more than 13 years.

P. vera is diagnosed by means of clinical criteria. The clinical picture includes headaches, pruritus, splenomegaly in two thirds of the patients, bleeding or thromboses, hypertension in a third of the patients, gout, which is brought about by an increase in the production of uric acid, and, in some cases, septic ulcers. The most important laboratory finding is an increase in the values for haemoglobin, haematocrit, erythrocyte count and total erythrocyte volume, and also a neutrophilic granulocytosis or thrombocytosis in many cases. Since, on the one hand, most of the criteria are rather diffuse and, on the other hand, not all the patients fulfil these criteria, it is frequently difficult to distinguish p. vera from other myeloproliferative diseases, such as chronic granulocytic leukaemia or essential thrombocytosis, and thereby confirm the diagnosis. To date, the molecular cause of p. vera is completely unknown. Since, however, p. vera takes a severe course if it is not treated, accurate diagnosis is important.

An object of the invention was therefore to find the molecular cause of polycythaemia rubra vera and to create the possibility of diagnosing it.

This object was achieved by isolating a gene which is expressed specifically in association with p. vera and not in healthy control individuals. This gene is designated the PRV-1 gene (polycythaemia rubra vera).

A similar nucleotide sequence is disclosed in International application WO 98/50552.

BRIEF DESCRIPTION OF THE DRAWINGS

FIG. 1 PRV-1 gene (SEQ ID NO: 1).

FIG. 2 PRV-1 protein (SEQ ID NO: 2).

DESCRIPTION OF THE INVENTION

One part of the subject-matter of the invention therefore relates to a polynucleotide which encodes the PRV-1 gene and essentially comprises the sequence ID No. 1. The polynucleotides of the present invention can be single-stranded or double-stranded DNA or RNA. If they are RNA, it is then clear to the skilled person that "U" nucleotides are present in place of "T" nucleotides. "Polynucleotide" is understood as meaning nucleic acids which contain 15 or more nucleotides.

The nucleotide sequence according to the invention is depicted in FIG. 1. The invention therefore relates to a polynucleotide which corresponds to the sequence shown in FIG. 1 and also to a polynucleotide whose nucleotide sequence exhibits minor differences. Within the meaning of the present application, minor differences are understood as meaning those sequences in which a few, preferably not more than 50 and particularly preferably not more than 25, nucleotides can be exchanged, with, however, the function of the gene encoded by the nucleotide sequence being unaffected. The skilled person is familiar with the fact that a base triplet encoding an amino acid can be replaced with another triplet which encodes the same amino acid. In addition to this, regions which are of less importance can be deleted and/or mutated to a minor extent. In a particular embodiment, the polynucleotide comprises nucleotides 36 to 1346 of sequence No. 1, that is the coding region of the PRV-1 gene. Another embodiment comprises nucleotides 36 to 1262 of sequence No. 1. This region presumably encodes the active region of the PRV-1 polypeptide. Finally, the polynucleotide of the invention can also comprise nucleotides 39 to 1346 or 39 to 1262 of sequence No. 1, such that the codon which encodes the starting methionine is not present. A preferred embodiment is a polynucleotide which comprises nucleotides 99–1346 or 99 to 1262 of sequence No. 1. This results in the codons at the 5' end which encode the signal peptide of the PRV-1 polypeptide not being present.

The polynucleotide according to the invention can also be a fragment of the PRV-1 gene. As a rule, the fragment possesses more than 100 nucleotides, preferably, however, more than 300 nucleotides. The fragments can also be used as primers or as probes, in particular for PCR; in this case, the fragments can be truncated to fit the purpose. Usually, primers have a length of between 10 and 30 nucleotides and probes have a length of between 15 and 50 nucleotides.

The PRV-1 gene is an endogenous gene whose expression in healthy individuals is, however, restricted to only a few organs. Normally, it is expressed in the main in the haematopoietic organs, i.e. in bone marrow and foetal liver, and weakly expressed in the spleen, but not expressed in heart, muscle, pancreas or kidney. In patients who are suffering from p. vera, this gene is very strongly overexpressed in the haematopoietic cells, in particular.

The PRV-1 gene encodes a protein which exhibits the protein sequence shown in FIG. 2. The signal peptide, which is present in the protein sequence of all surface molecules and normally removed when the protein is processed, is divided off by a hyphen. The protein has the sequence ID No. 2. Another aspect of the invention is consequently an essentially pure polypeptide having the sequence No. 2 or a polypeptide having the sequence No. 2 but lacking the signal peptide (i.e. amino acids 22 to 437 of sequence No. 2). Other embodiments encompass amino acids 1 to 409 or 22 to 409 of sequence No. 2 (what is probably the active region of the protein).

With regard to biological activity, the polypeptide according to the invention is preferably glycosylated; it is most preferably N-glycosylated. It can then be glycosylated at at least one of the amino acids Asn-46, Asn-189 and Asn-382 of the PRV-1 polypeptide (the amino acid numbers refer to the sequence No. 2) The invention also encompasses fragments of the polypeptides according to the invention which are N-glycosylated. The fragments are at least 50 amino acids in length, preferably at least 100 amino acids and most preferably at least 150 amino acids. In another embodiment, a polypeptide can be o-glycosylated.

It is clear to the skilled person that particular amino acids can be replaced with other amino acids without impairing the biological activity of the protein. Such modified forms of the polypeptides according to the invention are also part of the subject-matter of the invention. The amino acid replacements are those which do not have a negative effect on the biological activity of the protein. The skilled person can make use of well known rules for selecting the replacements.

Depending on the method of preparation, the PRV-1 polypeptide can, for example, possess a glycosyl phosphatidylinositol anchor. This is then bonded to the amino acids which correspond to amino acids 407 to 409 in sequence ID No. 2. A GPI anchor is used to anchor a protein by means of a lipid on the outside of the cell membrane. However, for reasons which have not so far been conclusively elucidated, it is frequently observed that GPI-linked proteins are also released into the medium. This is referred to as "shedding". To date, it has not been clarified whether this is a specific process, i.e. such proteins are cleaved from the membrane by enzymes in a controlled manner, or whether it represents a non-specific loss of the anchor. It is consequently very probable that PRV-1 is to be found both on the cell membrane and extracellularly. The secreted form, which is not membrane-bound, is probably more important for the effect of the polypeptide as a growth factor since, as a growth factor, this form is able to diffuse and reach other cells.

It is clear to the skilled person that he can influence the attachment of the protein to the cell membrane by manipulating these amino acids. This particularly concerns the preparation of defined DNA constructs which are intended for expressing the PRV-1 polypeptide or fragments of this polypeptide. The codons which encode these amino acids can be mutated or deleted.

The gene encodes a surface receptor of the uPAR/Ly6 family. This receptor family can transduce mitogenic signals, i.e. signals which stimulate cell division. It is therefore assumed that overexpression of the PRV-1 gene, inter alia on the granulocytes of p. vera patients, contributes to hyperproliferation of these cells.

It has been found that PRV-1 is not expressed on granulocytes in healthy individuals or in patients suffering from other myeloproliferative diseases, e.g. suffering from chronic granulocytic leukaemia, acute granulocytic leukaemia or essential thrombocytosis.

In order to be able to use the polypeptide encoded by the PRV-1 gene for analyses and detection methods, it is expediently generated from recombinant DNA, with the recombinant DNA preferably comprising the nucleotide sequence ID No. 1 or at least the coding region of the PRV-1 gene, that is nucleotides 36 to 1346 of sequence ID No. 1, at least, however, nucleotides 39 to 1262, functionally linked to a promoter. However, the recombinant DNA can also comprise only a fragment of sequence No. 1.

The invention furthermore relates to a vector which contains the recombinant DNA for the PRV-1 polypeptide, or a fragment thereof, and to a host cell which is transfected or transformed with this vector. The host cells may be prokaryotic, for example bacteria such as E. coli. However, the polypeptides which are expressed are then not glycosylated. Preference is therefore given to eukaryotic host cells, which are able to glycosylate the expressed protein post-translationally and modify it in other ways. Examples of eukaryotic host cells are insect cells, such as Sf9 cells, for expression following infection with recombinant baculoviruses, and mammalian cells, such as COS cells, CHO cells and HeLa cells. These examples are not exhaustive. It is also possible to use yeast cells as host cells. It is clear to the skilled person that the glycosylation pattern can differ depending on the host cell. The biological activity of the expression product can therefore also vary. Particular preference is given to host cells which glycosylate the expression product in such a way that the biological activity of the protein is retained.

The PRV-1 polypeptide which is isolated from granulocytes or produced recombinantly can be employed both for diagnosing polycythaemia vera and for treating the disease.

One therapeutic possibility is that of "antisense therapy". This method employs an "antisense" RNA molecule, that is an RNA which is complementary to the PRV RNA. Since the PRV-1 RNA has the sequence 5'-AAAAGCAGAAAGAGATTACCAGCC-3' (seq. ID No. 3) at its beginning, the requisite antisense RNA directed against this sequence would possess the following nucleotide sequence: 5'-GGCTGGTAATCTCTTTCTGCTTTT-3' (seq. ID No. 4). This antisense RNA is incorporated into a vector and introduced into the p. vera cells. This RNA is introduced, for example, by means of transfection, with the vector used for the transfection preferably being configured such that it is introduced specifically into the p. vera cells. Expression of the antisense RNA results in it no longer being possible for the PRV-1 mRNA to be translated into a polypeptide. Cells which have been treated in this way do not then form any PRV-1 protein.

The invention therefore also relates to a process for detecting p. vera which is characterized in that the PRV-1 polypeptide, or an epitope thereof, is detected and the extent of the expression is determined.

Overexpression of this receptor on mature cells outside of the bone marrow, e.g. on granulocytes, is a strong indication of the presence of the disease p. vera. This overexpression is expediently detected by means of an immunoassay using antibodies which are directed against the PRV-1 receptor. Suitable test methods are the known immunoassay variants which make use of PRV-1 polypeptide-specific antibodies together with other labelled antibodies which can be immobilized or in solution. The labelling can be effected in a manner known per se, for example using radioactive isotopes, by means of fluorescence or luminescence, using enzymes, by means of colour-forming reactions or using other groups which are suitable for the determination. These variants are known to the skilled person and do not require any more detailed explanation here. According to the invention, ELISA tests are particularly preferred.

The antibodies which are required for specifically detecting the PRV-1 receptor can likewise be prepared in a manner which is known per se. Both monoclonal and polyclonal antibodies are suitable, with preference being given to using monoclonal antibodies.

Peptides which are derived from the protein can also be used for preparing antibodies. Within the context of the present invention, success was achieved using the peptides having the sequences:

a) KVSDLPRQWTPKN (amino acids 34 to 46) [seq. ID No. 5], and b) SAREKRDVQPPASQH (amino acids 391 to 405) [seq. ID No. 6].

The polyclonal antibodies are normally produced by immunizing a suitable host (rabbit) with the PRV-1 polypeptide, where appropriate bound to an immunological support (adjuvant), and eliciting an immune response. Monoclonal antibodies can be generated in a manner known per se using the hybridoma technique. The antibodies can be purified by means of affinity purification. The preparation and purification of antibodies are described, for example, in "Antibodies: A Laboratory Manual" by Harlow and Lane, Cold Spring Harbor Laboratory Press.

Furthermore, such polyclonal or monoclonal antibodies which are directed against PRV-1 can also be used for treating the disease.

In another embodiment, the PRV-1 receptor can be detected using an RT-PCR method. For this, RNA is first of all isolated from the PRV-1-overexpressing cells, which are as a rule granulocytes. A reverse transcription is then performed in a manner known per se using an RT primer. The RT primer is preferably a primer which has the following nucleotide sequence (SEQ ID No. 7):

ATTAGGTTATGAGGTCAGAGGGAGGTT.

In this way, the specific PRV-1 RNA is transformed into DNA. This DNA is then amplified in a PCR reaction in a manner known per se. The following two primers are preferably employed for the amplification cycles:

As the sense primer (SEQ ID No. 8)

GCAGAAAGAGATTACCAGCCACAGACGG.

As the antisense primer (SEQ ID No. 9)

GAATCGTGGGGGTAATAGAGTTAGCAGG.

The skilled person is readily able to use the disclosed sequence to find other primers which are also suitable.

Since the RNA is used as the starting material for this method, the PCR signal is only positive when the PRV-1 gene is also expressed. As explained above, this is only the case when the patient is suffering from p. vera. PRV is not expressed in granulocytes of healthy patients. Consequently, the absence of any RT-PCR signal indicates that no p. vera is present.

In another alternative, it is also possible to use a blotting method, preferably a Northern Blot, for diagnosing p. vera. For such a method, the RNA is isolated from granulocytes and then examined for the expression of PRV-1 using a blotting method, for example Northern blotting. The cDNA sequence of SEQ ID No. 1, or a segment of the sequence, can be used as the probe. Hybridization then only occurs if the granulocytes are derived from a patient suffering from p. vera since only then is there any expression on the granulocytes. The absence of hybridization indicates that the individual from whom the granulocytes are derived does not have p. vera.

It is also possible to use a fragment of the gene for the Northern blot hybridization. Such a fragment is normally more than 100 bases in length, preferably more than 300 bases in length. Alternatively, various different fragments of the gene, which can be used as probes in the Northern blot, can be prepared by digesting the gene with restriction endonucleases. If the fragments are derived from the cDNA, they are then present as double strands which have to be separated into the single strands for the hybridization. Suitable examples are the Bam HI-PstI fragment from base pair 420 to base pair 831, or the PstI-PstI fragment from base pair 831 to base pair 1900.

PRV-1 mRNA, and consequently the expression of PRV-1, can also be detected by first of all reverse-transcribing the mRNA in an RT-PCR reaction and then amplifying the cDNA; the amplified DNA is then detected with a probe in a hybridization method.

In the case of a positive diagnosis, the disease has to be treated since it otherwise leads to death within a relatively short period of time. For this treatment, it is possible to use specific antibodies which are directed against PRV-1 and to which cytotoxic components can be bonded, where appropriate.

The invention therefore furthermore relates to a drug which, in addition to the customary excipients, comprises antibodies which are directed against the PRV-1 receptor.

Since the PRV-1 receptor is overexpressed in p. vera, many antibodies are bound on the surface of the affected granulocytes when they come into contact with the anti-PRV-1 antibody. The binding of many antibodies to these cells stimulates the immunological cells to destroy these granulocytes. In this way, it is possible to eliminate the p. vera cells specifically.

Surprisingly, it has also been found that the PRV-1 polypeptide exhibits haematopoietic activity. The PRV-1 polypeptide is able to stimulate certain haematopoietic precursor cells to form erythroid colonies. It is particularly the N-glycosylated PRV-1 polypeptides which display this function. The polypeptides according to the invention which are preferred are therefore the N-glycosylated PRV-1 polypeptides, and fragments thereof, which display the growth factor activity.

Another aspect of the invention is therefore a drug which, in addition to a pharmaceutically tolerated excipient, comprises the PRV-1 polypeptide or a biologically active fragment thereof. The PRV-1 polypeptide is preferably glycosylated PRV-1 polypeptide and, even more preferably, N-glycosylated PRV-1 polypeptide or a biologically active fragment thereof. The invention also relates to drugs which comprise at least one polynucleotide according to the invention.

The present invention furthermore relates to the use of PRV-1 polypeptide, or a biologically active fragment thereof, as a growth factor in vivo and ex vivo. The PRV-1 polypeptide, or a biologically active fragment thereof, can be used for treating all pancytopenias and pancytopathies in the bone marrow and in the circulation (change in the cellular constituents of the peripheral blood and bone marrow). The polypeptides of the present invention can, for example, be used for treating anaemias in the case of kidney failure, chemotherapy or whole body radiation, for treating neutropenias and thrombocytopenias during chemotherapy or whole body radiation, for the ex-vivo treatment of peripheral or bone marrow stem cells for expansion (multiplication) and retransfusion into the patients, and for treating sepsis, systemic inflammatory response syndrome (SIRS) or regional inflammatory reactions. The polypeptides of the present invention, or drugs which comprise them, can be administered in a wide variety of ways. The forms of administration comprise intravenous, intramuscular, subcutaneous, intraperitoneal, oral, transdermal and transmucosal administration.

The polynucleotides according to the invention can also be used for treating pancytopenias and pancytopathies. In this case, the aim is to express a PRV-1 polypeptide, or a functional fragment thereof, in cells of the affected patient. Gene therapy methods are first and foremost used in this connection. Cells can be isolated from the patient and transfected with a polynucleotide according to the invention (ex-vivo manipulation), after which they are then returned to the patient. It is also possible to conceive of methods in which the polynucleotides according to the invention gain access into the target cells by means of viral transfer. Expression of the inserted nucleic acids then leads to haematopoietic activity.

The invention also relates to kits for detecting either polycythaemia vera or disturbances of the haematopoietic system. These kits comprise a polynucleotide according to the invention and/or a polypeptide according to the invention and/or one or more antibodies according to the invention. In addition to this, the kit can also comprise a container or compositions which are suitable for implementing detection reactions. Examples of such compositions are buffer solutions, reagents for blocking membranes, hybridization solutions, secondary antibodies, substrate solutions for detection reactions, etc. The kit is preferably used for implementing PCR reactions, Northern blots, Southern blots, Western blots and ELISA, RIA or similar reactions.

The following examples are given in explanation.

EXAMPLES

Example 1
Characterizing the PRV Gene

The following experiments were carried out in order to characterize the gene:

the following protocol was used to isolate granulocytes from stored blood or from blood obtained by bleeding p. vera patients:

an equal volume of 3% dextran solution in 0.9% NaCl was added to the blood and the mixture was left to stand at room temperature (RT) for 20 minutes.

The mixture separated into two phases. The upper, light-coloured phase was removed and centrifuged for 10 minutes at 1800 g and at RT.

The supernatant was discarded and the cell pellet was resuspended in the same volume of 0.9% NaCl.

In each case 35 ml of the cells in NaCl were layered on 15 ml of Ficoll-Hypaque.

The cells on the Ficoll-Hypaque were then centrifuged for 60 minutes at 1800 g and at RT without using the brake.

A cell pellet and two layers with an interphase were formed.

The layers and interphase were aspirated off and the cell pellet was resuspended for 30 seconds in 10 ml of ice-cold 0.2% NaCl, and 10 ml of ice-cold 1.6% NaCl were added immediately after 30 seconds.

The cells were centrifuged down for 10 minutes at 1800 g and at RT.

They were then washed once in 10 ml of PBS and centrifuged down.

The cell pellet contained 95–99%-pure granulocytes.

RNA was isolated from these cells using standard methods.

10 mg of this RNA were examined for the expression of PRV-1 in a Northern blot. The entire cDNA sequence shown in SEQ ID No. 1 was used as a probe.

This experiment was performed on 19 p. vera patients and 21 control samples of stored blood. The PRV-1 probe was found to hybridize strongly in the case of the p. vera patients. No hybridization was observed in healthy control samples.

Example 2
PRV-1 possesses Growth Factor Activity

Embryos were removed from a pregnant mouse 13.5 days after fertilization. The foetal livers were removed. The cells contained in them were stained using antibodies and enriched for particular cells, and depleted for other cell types, by means of column chromatography. This results in a cell mixture which is enriched for certain haematopoietic precursor cells (colony forming units-erythroid, CFU-E). Thus, while in all approximately 2% of the foetal liver consists of CFU-E, 30–40% of the enriched cells consist of CFU-E.

These CFU-Es were transfected using a retrovirus. To do this, a packaging cell line, designated 293-T, was itself transfected 48 hours previously. 293-T cells are an established human embryonic kidney cell line. 293-T cells are stably transfected with several genes from a retrovirus. If these 293-T cells are now transfected with two plasmids, termed pOS and pKAT, the 293-T cells then produce a retrovirus which is able to infect murine foetal liver cells. If the 293-T cells are transfected with an empty pOS vector and PKAT, a wild-type retrovirus, which only expresses retroviral proteins, is then produced. On the other hand, cloning a human gene, e.g. PRV-1, into the pOS vector results in the production of a retrovirus which expresses this protein when it has infected cells. The 293-T cells secrete the retrovirus into the cell culture medium.

After two days, the cell culture medium from the transfected 293-T cells which contains the retrovirus is harvested and filtered once through a 0.45 μm filter. In order to transfect the foetal liver cells, these latter cells are mixed with the filtered cell culture medium, which contains the retrovirus, and centrifuged for 2 hours at 1800 rpm and 20° C. in the added presence of Polybren. The transfected foetal liver cells were then cultured in a medium (Methocult, from Cell Systems) which contains, in addition to the usual salts and amino acids, foetal calf serum, 0.0001–0.4 IU of erythropoeitin (EPO)/ml and methyl cellulose (0.8%). The CFU-Es require EPO in order to form haematopoietic colonies. The methyl cellulose solidifies the medium in the form of a jelly, thereby fixing individual cells in this jelly so that, in contrast to being in a liquid medium, they cannot move. It is therefore possible to observe whether a haematopoietic colony is or is not formed from a single cell. CFU-Es form erythroid colonies, that is colonies which contain red blood cells and their precursor cells.

After three days, a count is taken of the number of haematopoietic colonies which have developed. Various mixtures are compared. The mixtures were not all examined in each experiment; mixtures 1–3 are very similar controls and each of them can be compared individually with mixture 4.

TABLE 1

The table lists the results obtained from three experiments which were performed as described. The figures in each case indicate the number of colonies

| | Mixture 1 un-transfected | Mixture 2 empty vector (pOS) | Mixture 3 GFP (pOS-GFP) | Mixture 4 PRV-1 (pOS-PRV-1) |
|---|---|---|---|---|
| Experiment 1 | 116 | 156 | 80 | 326 |
| Experiment 2 | | 271 | 273 | 410 |
| Experiment 3 | 120 | | 131 | 291 |

Mixture 1: Cells which were not transfected with a retrovirus;
Mixture 2: Cells which were transfected with an empty pOS vector;
Mixture 3: Cells which were transfected with a "green fluorescent protein" (GFP), a protein which is not haematopoietically active.
Mixture 4: Cells which were transfected with pOS-PRV-1 (vector + gene according to the invention).

The experiments demonstrate that CFU-Es which were transfected with PRV-1 form very many more colonies (up to three times as many) than do the various control CFU-Es. This result indicates that PRV-1 is a growth factor for CFU-E.

Example 3
Solubility of the PRV-1 Growth Factor

A further experiment was carried out in order to investigate whether PRV-1 is a soluble growth factor or whether cell-cell contact is required. It is not only a retrovirus which is produced by the packaging cell line 293-T after it has been transfected with the pOS and pKAT vectors. In addition, the 293-T cells also synthesize the protein encoded by the gene cloned in pOS, i.e. PRV-1 in the present case. If the gene product is a soluble protein, it is secreted into the medium which surrounds the packaging cell line 293-T. If the 293-T cells are transfected only with the pOS vector, without pKAT, no retroviruses are then formed. The cell culture medium then only contains the soluble protein produced by the cells. Medium which is derived from pOS-PRV-1-transfected cells, and which does not contain any retrovirus, is mixed with CFU-Es and the whole is plated out in the methyl cellulose medium; the resulting colonies are then counted.

The following results were obtained:

TABLE 2

Solubility of PRV-1. The figures in each case indicate the number of colonies.

| | Mixture 1 un-transfected | Mixture 2 empty vector (pOS) | Mixture 3 GFP (pOS-GFP) | Mixture 4 PRV-1 (pOS-PRV-1) |
|---|---|---|---|---|
| Experiment 4 | | 137 | 187 | 557 |

In this experiment, too, CFU-Es which were treated with PRV-1-containing medium formed very many more haematopoietic colonies than did control cells. It can be concluded from this result that PRV-1 is a soluble growth factor.

Example 4

The Growth Factor PRV-1 is N-glycosylated

Granulocytes were isolated from a patient suffering from p. vera, and protein extracts were prepared from these cells using a standard protocol. These protein extracts were treated in accordance with the protocol for the "N-Glycosidase F Deglycosylation Kit" supplied by Boehringer Mannheim. In detail, this means that a "denaturation buffer" was added to the protein extracts and the mixtures were heated at 95° C. for 3 minutes, after which they were treated either with "reaction buffer" or with "reaction buffer" plus N-glycosidase. Each mixture was incubated overnight at 37° C. and the proteins were analysed on a PAGE gel electrophoresis followed by a Western blot. The PRV-1 protein was detected with an antibody directed against a protein having the amino acid sequence ID No. 5. The results show that while PRV-1 protein purified from granulocytes is 60–65 kDa in size, it is only 40 kDa in size after having been digested with N-glycosidase. This clearly proves that PRV-1 is glycosylated on asparagine residues (asparagine=N).

What is claimed is:

1. An isolated polypeptide, comprising one of the following amino acid sequences:
   amino acids 1–437 of SEQ. ID NO.: 2;
   amino acids 1–409 of SEQ. ID NO.: 2;
   amino acids 22–437 of SEQ. ID NO.: 2;
   amino acids 22–409 of SEQ. ID NO.: 2;
   or a antigenic fragment thereof containing at least 50 amino acids.

2. An isolated polypeptide, comprising one of the following amino acid sequences:
   amino acids 1–437 of SEQ. ID NO.: 2;
   amino acids 1–409 of SEQ. ID NO.: 2;
   amino acids 22–437 of SEQ. ID NO.: 2; or
   amino acids 22–409 of SEQ. ID NO.: 2.

3. An isolated polypeptide comprising the amino acid sequence of SEQ. ID NO.: 2.

4. An isolated polynucleotide, comprising one of the following nucleotide sequences:
   nucleotides 1–1600 of SEQ. ID NO.: 1;
   nucleotides 36–1346 of SEQ. IDNO.: 1;
   nucleotides 36–1262 of SEQ. ID NO.: 1;
   nucleotides 39–1346 of SEQ. ID NO.: 1;
   nucleotides 39–1262 of SEQ. ID NO.: 1;
   nucleotides 99–1346 of SEQ. ID NO.: 1; or
   nucleotides 99–1262 of SEQ. ID NO.: 1.

5. Recombinant DNA which comprises a polynucleotide according to claim 4.

6. Recombinant DNA according to claim 5, characterized in that the nucleotide sequence is functionally linked to a promoter.

7. Expression vector, containing the recombinant DNA according to claim 5.

8. Transformed or transfected host cell which contains a polynucleotide according to claim 4.

9. Antibody against a polypeptide of claim 1, or an epitope thereof.

10. Antibody according to claim 9, characterized in that it is a monoclonal antibody.

11. An isolated polypeptide of claim 1, which is N-glycosylated.

12. An isolated polypeptide of claim 2, which is N-glycosylated.

13. A method of increasing the production of red blood cells in a host in need thereof, comprising,
    administering an amount of a polypeptide of claim 2 which is effective for increasing said red blood cell production.

14. A method of claim 13, wherein said polypeptide comprises amino acids 1–437 of SEQ ID NO: 2.

15. A method of claim 13, wherein said polypeptide comprises 22–437 of SEQ ID NO: 2.

16. A method of claim 14, wherein said polypeptide is N-glycosylated.

17. A method of claim 15, wherein said polypeptide is N-glycosylated.

18. A method of diagnosing polycythaemia vera in a human subject, comprising, detecting expression of a polynucleotide coding for human PRV-1 in a blood sample comprising granulocytes, whereby the presence of said expressed polynucleotide in said cells is diagnostic of polycythaemia vera.

19. A method of claim 18, wherein said polynucleotide coding for human PRV-1 comprises the polynucleotide sequence of SEQ ID NO: 1.

20. A method of claim 18, wherein said polynucleotide coding for human PRV-1 comprises the polypeptide sequence of SEQ ID NO: 2.

21. A method of claim 18, wherein the detecting is performed by RT-PCR or a blotting method.

* * * * *

SEQUENCE LISTING

<160> NUMBER OF SEQ ID NOS: 9

<210> SEQ ID NO 1
<211> LENGTH: 1600
<212> TYPE: DNA
<213> ORGANISM: Homo sapiens

<400> SEQUENCE: 1

```
aaaagcagaa agagattacc agccacagac gggtcatgag cgcggtatta ctgctggccc      60
tcctggggtt catcctccca ctgccaggag tgcaggcgct gctctgccag tttgggacag     120
ttcagcatgt gtggaaggtg tccgacctgc cccggcaatg gaccctaag aacaccagct      180 gcgacagcgg cttggggtgc caggacacgt tgatgctcat tgagagcgga ccccaagtga     240
gcctggtgct ctccaagggc tgcacggagg ccaaggacca ggagcccgc gtcactgagc      300 accggatggg ccccggcctc tccctgatct cctacacctt cgtgtgccgc caggaggact     360
tctgcaacaa cctcgttaac tccctcccgc tttgggcccc acagccccca gcagacccag     420
gatccttgag gtgcccagtc tgcttgtcta tggaaggctg tctggagggg acaacagaag     480
agatctgccc caaggggacc acacactgtt atgatggcct cctcaggctc agggaggag      540 gcatcttctc caatctgaga gtccagggat gcatgcccca gccaggttgc aacctgctca     600
atgggacaca ggaaattggg cccgtgggta tgactgagaa ctgcaatagg aaagattttc     660
tgacctgtca tcggggacc accattatga cacacgaaa cttggctcaa gaacccactg      720
attggaccac atcgaatacc gagatgtgcg aggtggggca ggtgtgtcag gagacgctgc     780
tgctcataga tgtaggactc acatcaaccc tggtggggac aaaaggctgc agcactgttg     840
```

-continued

```
gggctcaaaa ttcccagaag accaccatcc actcagcccc tcctggggtg cttgtggcct      900
cctataccca cttctgctcc tcggacctgt gcaatagtgc cagcagcagc agcgttctgc      960
tgaactccct ccctcctcaa gctgcccctg tcccaggaga ccggcagtgt cctacctgtg     1020
tgcagcccct tggaacctgt tcaagtggct ccccccgaat gacctgcccc aggggcgcca     1080
ctcattgtta tgatgggtac attcatctct caggaggtgg gctgtccacc aaaatgagca     1140
ttcagggctg cgtggcccaa ccttccagct tcttgttgaa ccacaccaga caaatcggga     1200
tcttctctgc gcgtgagaag cgtgatgtgc agcctcctgc ctctcagcat gagggaggtg     1260
gggctgaggg cctggagtct ctcacttggg gggtggggct ggcactggcc ccagcgctgt     1320
ggtggggagt ggtttgccct tcctgctaac tctattaccc ccacgattct tcaccgctgc     1380
tgaccaccca cactcaacct ccctctgacc tcataaccta atggccttgg acaccagatt     1440
ctttcccatt ctgtccatga atcatcttcc ccacacacaa tcattcatat ctactcacct     1500
aacagcaaca ctggggagag cctggagcat ccggacttgc cctatgggag agggacgct     1560 ggaggagtgg ctgcatgtat ctgataatac agaccctgtc                           1600
```

<210> SEQ ID NO 2
<211> LENGTH: 437
<212> TYPE: PRT
<213> ORGANISM: Homo sapiens

<400> SEQUENCE: 2

```
Met Ser Ala Val Leu Leu Ala Leu Leu Gly Phe Ile Leu Pro Leu
  1               5                  10                  15

Pro Gly Val Gln Ala Leu Leu Cys Gln Phe Gly Thr Val Gln His Val
                 20                  25                  30

Trp Lys Val Ser Asp Leu Pro Arg Gln Trp Thr Pro Lys Asn Thr Ser
                 35                  40                  45

Cys Asp Ser Gly Leu Gly Cys Gln Asp Thr Leu Met Leu Ile Glu Ser
         50                  55                  60

Gly Pro Gln Val Ser Leu Val Leu Ser Lys Gly Cys Thr Glu Ala Lys
 65                  70                  75                  80

Asp Gln Glu Pro Arg Val Thr Glu His Arg Met Gly Pro Gly Leu Ser
                 85                  90                  95

Leu Ile Ser Tyr Thr Phe Val Cys Arg Gln Glu Asp Phe Cys Asn Asn
                100                 105                 110

Leu Val Asn Ser Leu Pro Leu Trp Ala Pro Gln Pro Ala Asp Pro
             115                 120                 125

Gly Ser Leu Arg Cys Pro Val Cys Leu Ser Met Glu Gly Cys Leu Glu
 130                 135                 140

Gly Thr Thr Glu Glu Ile Cys Pro Lys Gly Thr Thr His Cys Tyr Asp
145                 150                 155                 160

Gly Leu Leu Arg Leu Arg Gly Gly Gly Ile Phe Ser Asn Leu Arg Val
                165                 170                 175

Gln Gly Cys Met Pro Gln Pro Gly Cys Asn Leu Leu Asn Gly Thr Gln
                180                 185                 190

Glu Ile Gly Pro Val Gly Met Thr Glu Asn Cys Asn Arg Lys Asp Phe
            195                 200                 205

Leu Thr Cys His Arg Gly Thr Thr Ile Met Thr His Gly Asn Leu Ala
        210                 215                 220

Gln Glu Pro Thr Asp Trp Thr Ser Asn Thr Glu Met Cys Glu Val
225                 230                 235                 240
```

Gly Gln Val Cys Gln Glu Thr Leu Leu Ile Asp Val Gly Leu Thr
                245                 250                 255

Ser Thr Leu Val Gly Thr Lys Gly Cys Ser Thr Val Gly Ala Gln Asn
            260                 265                 270

Ser Gln Lys Thr Thr Ile His Ser Ala Pro Pro Gly Val Leu Val Ala
        275                 280                 285

Ser Tyr Thr His Phe Cys Ser Ser Asp Leu Cys Asn Ser Ala Ser Ser
    290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
                325                 330                 335

Ser Gly Ser Pro Arg Met Thr Cys Pro Arg Gly Ala Thr His Cys Tyr
            340                 345                 350

Asp Gly Tyr Ile His Leu Ser Gly Gly Leu Ser Thr Lys Met Ser
        355                 360                 365

Ile Gln Gly Cys Val Ala Gln Pro Ser Ser Phe Leu Leu Asn His Thr
    370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Ala Glu Gly Leu Glu Ser Leu
                405                 410                 415

Thr Trp Gly Val Gly Leu Ala Leu Ala Pro Ala Leu Trp Trp Gly Val
            420                 425                 430

Val Cys Pro Ser Cys
        435

<210> SEQ ID NO 3
<211> LENGTH: 24
<212> TYPE: DNA
<213> ORGANISM: Homo sapiens

<400> SEQUENCE: 3
aaaagcagaa agagattacc agcc                                              24

<210> SEQ ID NO 4
<211> LENGTH: 24
<212> TYPE: DNA
<213> ORGANISM: Homo sapiens

<400> SEQUENCE: 4
ggctggtaat ctctttctgc tttt                                              24

<210> SEQ ID NO 5
<211> LENGTH: 13
<212> TYPE: PRT
<213> ORGANISM: Homo sapiens

<400> SEQUENCE: 5

Lys Val Ser Asp Leu Pro Arg Gln Trp Thr Pro Lys Asn
  1               5                  10

<210> SEQ ID NO 6
<211> LENGTH: 15
<212> TYPE: PRT
<213> ORGANISM: Homo sapiens

```
<400> SEQUENCE: 6

Ser Ala Arg Glu Lys Arg Asp Val Gln Pro Pro Ala Ser Gln His
 1               5                  10                  15

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
attaggttat gaggtcagag ggaggtt                                          27

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 8
gcagaaagag attaccagcc acagacgg                                         28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 9
gaatcgtggg ggtaatagag ttagcagg                                         28
```